United States Patent [19]
Morooka et al.

[11] 4,069,230
[45] Jan. 17, 1978

[54] PREPARATION OF INDOLE DERIVATIVES

[75] Inventors: Shigeaki Morooka, Nishinomiya; Katsumi Tamoto; Akira Matuura, both of Takarazuka, all of Japan

[73] Assignee: Sumitomo Chemical Company, Limited, Osaka, Japan

[21] Appl. No.: 691,777

[22] Filed: June 1, 1976

[30] Foreign Application Priority Data

June 4, 1975 Japan .................................. 50-67765
June 9, 1975 Japan .................................. 50-70056

[51] Int. Cl.² ........................................ C07D 209/04
[52] U.S. Cl. ........................... 260/319.1; 260/326.15; 260/326.16
[58] Field of Search ..................... 260/319.1

[56] References Cited
U.S. PATENT DOCUMENTS 3,632,573   1/1972   Yamamoto et al. ............... 260/239.3
3,790,596   2/1974   Suvorov et al. ................. 260/319.1

OTHER PUBLICATIONS

Sundberg, The Chemistry of Indoles, pp. 148-158 and 208-213, 1970 Academic Press, N. Y. and London.

Primary Examiner—Ethel G. Love
Attorney, Agent, or Firm—Stevens, Davis, Miller & Mosher

[57] ABSTRACT

An improved process for preparing indole derivatives of the formula,

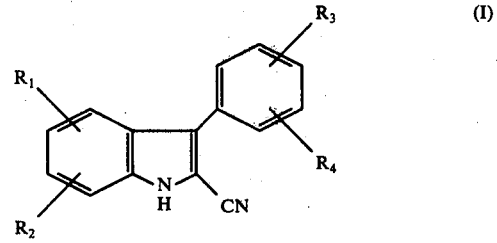

wherein $R_1$ and $R_2$ each are hydrogen, halogen, $C_1$–$C_3$ alkyl, $C_1$–$C_3$ alkoxy, nitro, cyano or trifluoromethyl, or when taken together, form methylenedioxy; $R_3$ is hydrogen, halogen, $C_1$–$C_3$ alkyl, $C_1$–$C_3$ alkoxy, nitro, cyano or dimethylamino; and $R_4$ is hydrogen or halogen, which comprises cyclizing a compound of the formula,

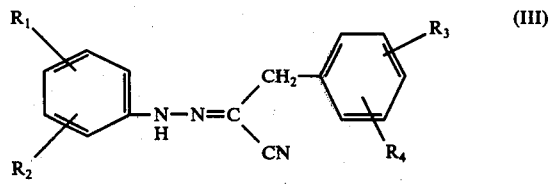

wherein $R_1$, $R_2$, $R_3$ and $R_4$ are as defined above, with an acidic condensing agent.

The indole derivatives of the formula (I) mentioned above are useful as a key intermediate for the preparation of benzodiazepines, which are useful as tranquilizers, muscle relaxants and the like.

7 Claims, No Drawings

PREPARATION OF INDOLE DERIVATIVES

The present invention relates to a process for preparing indole derivatives. More particularly, the invention pertains to a process for producing indole derivatives represented by the formula,

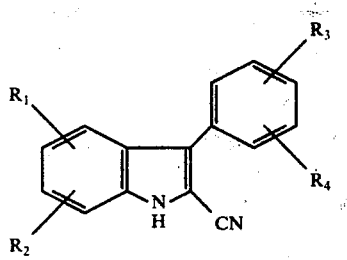
(I)

wherein $R_1$ and $R_2$ each are hydrogen, halogen, $C_1$–$C_3$ alkyl, $C_1$–$C_3$ alkoxy, nitro, cyano or trifluoromethyl or, when taken together, form methylenedioxy; $R_3$ is hydrogen, halogen, $C_1$–$C_3$ alkyl, $C_1$–$C_3$ alkoxy, nitro, cyano or dimethylamino; and $R_4$ is hydrogen or halogen.

Examples of $C_1$–$C_3$ alkyl are methyl, ethyl or n-propyl, and examples of $C_1$–$C_3$ alkoxy are methoxy, ethoxy or n-propoxy, and examples of halogen are fluorine, chlorine or bromine.

The indole derivatives represented by the formula (I) are characterized by the substituents of both cyano at the 2-position and aryl at the 3-position.

The present indole derivatives of the formula (I) are useful as intermediates for several medicines or pesticides. Thus, the indole derivatives (I) are already known as a key intermediate for the production of benzodiazepine derivatives of the following formula (II), which are useful as tranquilizers, muscle relaxants, anticonvulsants and hypnotics.

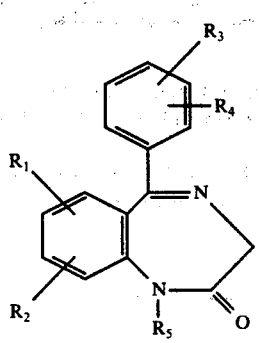
(II)

wherein $R_1$, $R_2$, $R_3$ and $R_4$ each are as defined above, and $R_5$ is hydrogen or lower alkyl, as disclosed, for example, in British Pat. Nos. 1210568 or 1253368.

Furthermore, the indole derivatives per se are also found to be useful as anti-microbial agents.

As for preparing the indole derivatives of the formula (I), only a few processes have been reported. For instance, such processes as described below are known:

Method A.

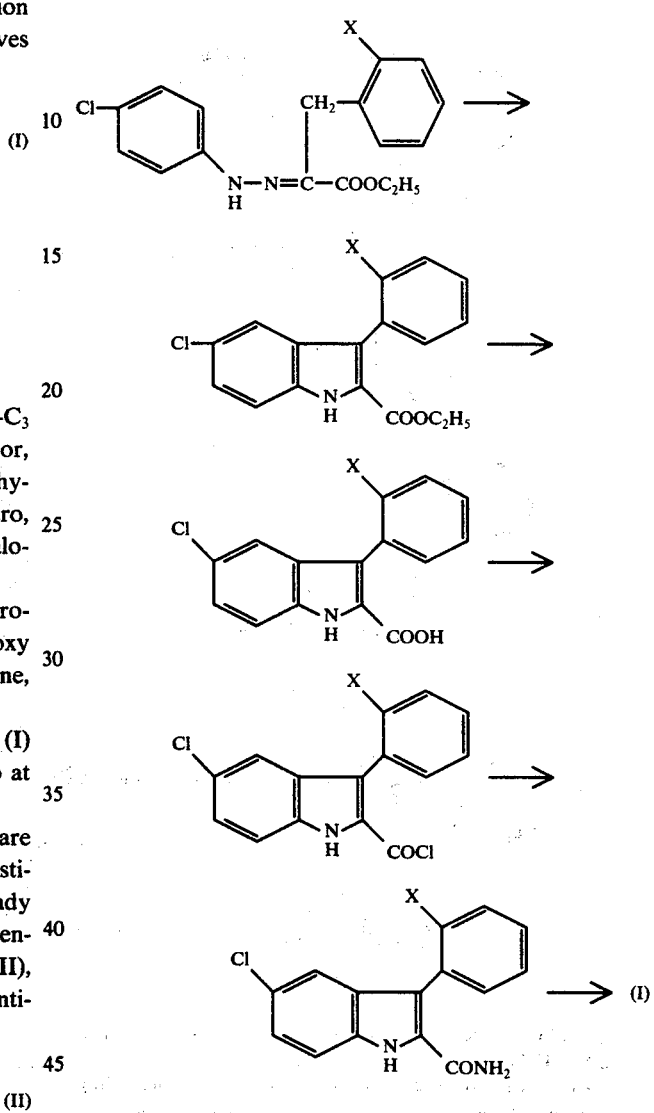

wherein X represents hydrogen, fluorine or chlorine.

[Ishizumi et. al., Chem. Pharm. Bull., Vol. 19, No. 2, 263 – 272 (1971)]

Method B.

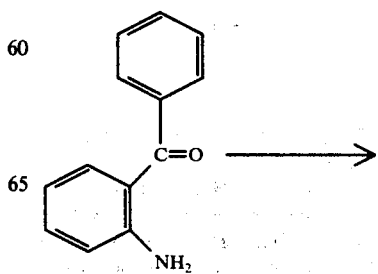

-continued

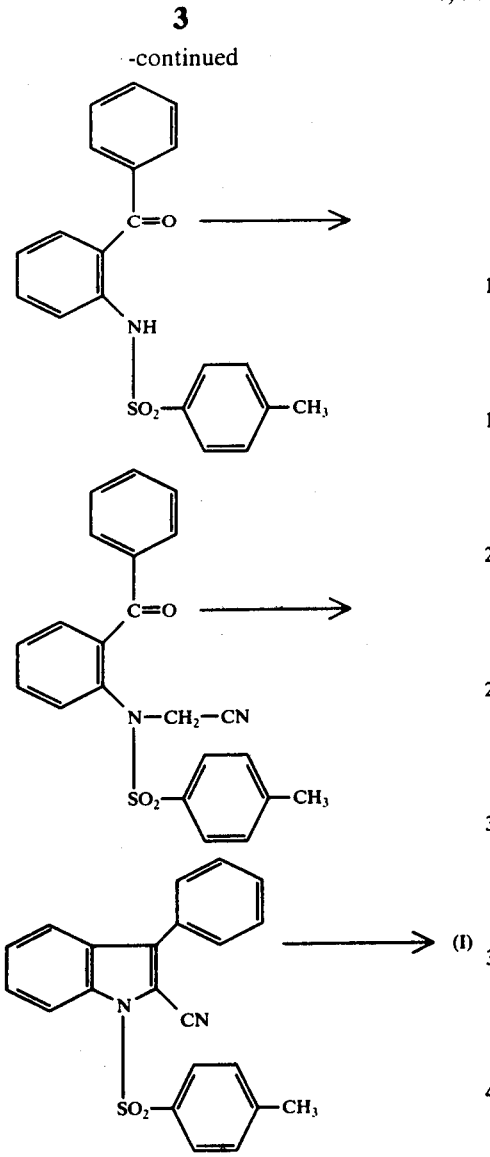

[Charles D. Jones, J. Org. Chem., Vol. 37, No. 23, 3624 − 3625 (1972)]

These known methods are, however, time-consuming and troublesome because five or four steps of reactions must be carried out to obtain the objective indole derivatives, and the starting materials used in the Method B are not so commonly available.

As a result of studies, we have found a more advantageous process for preparing the indole derivatives of the formula (I), which comprises cyclizing a compound of the formula,

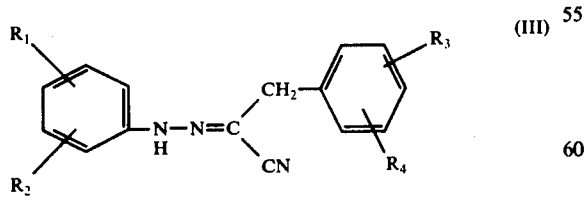

(III)

wherein $R_1$, $R_2$, $R_3$ and $R_4$ are as defined above, with an acidic condensing agent.

Contrary to the known processes, the process of this invention comprises only one step. Moreover, the hydrazone derivatives as the starting material of this process are easily obtained by the reaction between a cyanoacetic ester derivative (IV) and a diazonium salt of an aniline derivative (V) as shown in the following scheme:

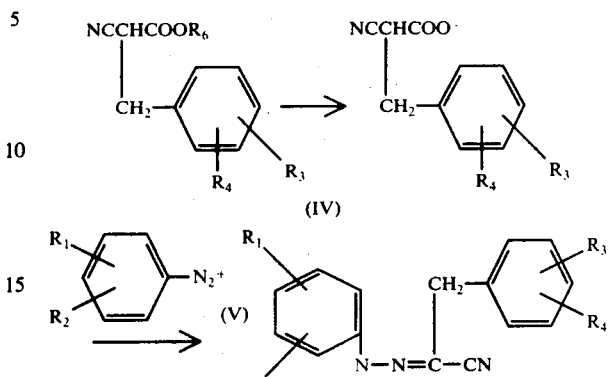

wherein $R_1$, $R_2$, $R_3$ and $R_4$ each are as defined above, and $R_6$ is alkyl.

The process of this invention involves the Fischer indole synthesis as its basic principle.

Although several applications of the Fischer indole synthesis to the preparation of an indole skelton are well known, there has been no report in which the Fischer indole synthesis is applied to the preparation of such indole derivatives as have cyano at the 2-position.

The present process applies for the first time the Fischer indole synthesis to the preparation of the indole derivatives having cyano at the 2-position.

In this process, the cyano group of the hydrazone derivatives is held in the indole derivatives.

It was surprising that the cyano group had remained intact in the present Fischer indole synthesis, because it was well known that the cyano group was generally susceptible under the conditions employed in the Fischer indole synthesis. For instance, (C):

A cyano group is readily hydrolyzed under an acidic condition.

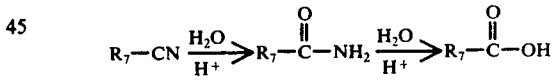

[Z. Rappoport, The Chemistry of the Cyano Group, page 256 (Interscience Publishers, New York, 1970)] (D):

In the presence of an acid, an alcohol easily adds to a cyano group to give an imino-ether.

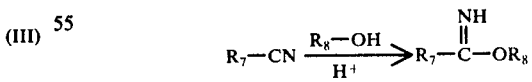

[Idem, ibid, page 263]

wherein $R_7$ is alkyl or aryl and $R_8$ is alkyl.

According to the present invention, indole-2-carbonitrile derivatives represented by the formula (I) are obtained in a high yield by cyclizing hydrazone derivatives of formula (II), in the presence of a suitable acidic condensing agent with or without solvent.

Suitable condensing agents include, for example, an inorganic acid such as hydrogen chloride, hydrogen bromide, sulfuric acid and polyphosphoric acid.

Examples of the solvent include water, methanol, ethanol, isopropanol, n-butanol and acetic acid. Above all, a combination of a lower alcohol and a hydrogen halide, in spite of being under the said imino-etherification condition, gives the indole-2-carbonitrile in particularly high yields.

The reaction temperature may be about 0° to 200° C, and favorably about 50° to 150° C.

According to the process of the present invention, there are obtained, for example, the following indole derivatives:

3-Phenyl-5-bromoindole-2-carbonitrile
3-Phenyl-5-methoxyindole-2-carbonitrile
3-Phenyl-5-nitroindole-2-carbonitrile
3-Phenyl-5-methylindole-2-carbonitrile
3-Phenyl-6-trifluoromethylindole-2-carbonitrile
3-Phenyl-6-chloroindole-2-carbonitrile
3-Phenyl-7-cyanoindole-2-carbonitrile
3-(o-Fluorophenyl)-5-methoxyindole-2-carbonitrile
3-(o-Fluorophenyl)-5-nitroindole-2-carbonitrile
3-(o-Chlorophenyl)-5-chloroindole-2-carbonitrile
3-(o-Chlorophenyl)-5-nitroindole-2-carbonitrile
3-(m-Nitrophenyl)-5-chloroindole-2-carbonitrile
3-(p-Methylphenyl)-5,6-methylenedioxyindole-2-carbonitrile
3-(p-Methoxyphenyl)-6-fluoroindole-2-carbonitrile
3-(p-Dimethylaminophenyl)-5-chloroindole-2-carbonitrile
3-(p-Cyanophenyl)-5-chloroindole-2-carbonitrile This invention is further disclosed in the following examples of more preferred embodiments thereof, which are presented for the purpose of illustration and it is not intended to limit the scope of the invention.

EXAMPLE 1

Into a solution of 4.0 g of phenylpyrvonitrile-p-chlorophenylhydrazone in 12 ml of isopropanol, gaseous hydrogen chloride was introduced and the mixture was refluxed for 2 hours. After cooling, the deposited crystals were filtered, washed with ample water and dried to give 3.6 g of 3-phenyl-5-chloroindole-2-carbonitrilè as white needles, m.p. 216°-217° C.

EXAMPLE 2

To 4 g of o-fluorophenylpyrvonitrile-p-chlorophenylhydrazone, 20 ml of 10% hydrogen chloride in ethanol was added and the mixture was refluxed for 2 hours on a water bath.

After cooling, precipitated crystals were filtered, washed with water and dried to give 3.5 g of 3-(o-fluorophenyl)-5-chloroindole-2-carbonitrile as pale brown powder melted at 185°-186° C.

EXAMPLE 3

Into a suspension of 5.0 g of phenylpyrvonitrile-p-bromophenylhydrazone in 15 ml of acetic acid, 1.0 g of dry hydrogen chloride gas was introduced below 20° C. The resulting suspension was heated at 100° C for 2 hours, and then concentrated under reduced pressure.

To the resulting oily residue, was added a mixture of toluene and water and the precipitated crystals were filtered to give 4.2 g of 3-phenyl-5-bromoindole-2-carbonitrile, m.p. 227°-230° C.

The following compounds are obtained similarly:

|  | Melting point |
|---|---|
| 3-Phenyl-5-methoxyindole-2-carbonitrile | 152-154° C |

-continued

|  | Melting point |
|---|---|
| 3-Phenyl-5-nitroindole-2-carbonitrile | 261-263° C |
| 3-Phenyl-5-methylindole-2-carbonitrile | 180-183° C |
| 3-Phenyl-6-trifluoromethylindole-2-carbonitrile | 143-145° C |
| 3-Phenyl-6-chloroindole-2-carbonitrile | 235-238° C |
| 3-Phenyl-7-cyanoindole-2-carbonitrile | Above 250° C |
| 3-Phenyl-5,7-dichloroindole-2-carbonitrile | 229-230° C |
| 3-(o-Fluorophenyl)-5-methoxyindole-2-carbonitrile | 166-167° C |
| 3-(o-Fluorophenyl)-5-nitroindole-2-carbonitrile | 148.5-150.5° C |
| 3-(o-Chlorophenyl)-5-chloroindole-2-carbonitrile | 162-164° C |
| 3-(o-Chlorophenyl)-5-nitroindole-2-carbonitrile | 218.5-220° C |
| 3-(m-Nitrophenyl)-5-chloroindole-2-carbonitrile | Above 250° C |
| 3-(p-Methoxyphenyl)-6-fluoroindole-2-carbonitrile | 225-226° C |
| 3-(p-Dimethylaminophenyl)-5-chloroindole-2-carbonitrile | 150-153° C |
| 3-(p-Cyanophenyl)-5-chloroindole-2-carbonitrile | Above 250° C |
| 3-(p-Methylphenyl)-5,6-methylenedioxyindole-2-carbonitrile | 248-249.5° C |

What is claimed is:

1. A process for producing indole derivatives of the formula,

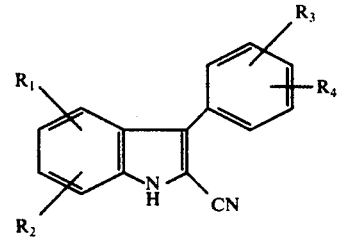

wherein $R_1$ and $R_2$ each are hydrogen, halogen, $C_1$-$C_3$ alkyl, $C_1$-$C_3$ alkoxy, nitro, cyano or trifluoromethyl or, when taken together, form methylenedioxy; $R_3$ is hydrogen, halogen, $C_1$-$C_3$ alkyl, $C_1$-$C_3$ alkoxy, nitro, cyano or dimethylamino; and $R_4$ is hydrogen or halogen, which comprises cyclizing a hydrazone derivative of the formula,

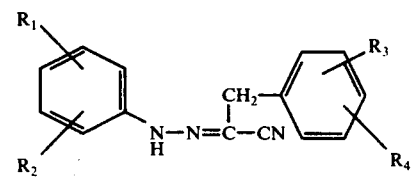

wherein $R_1$, $R_2$, $R_3$ and $R_4$ are as defined above, with an acidic condensing agent.

2. The process according to claim 1, wherein the reaction is effected in a solvent.

3. The process according to claim 2, wherein the solvent is methanol, ethanol, propanol or acetic acid.

4. The process according to claim 1, wherein the reaction is carried out in the presence of hydrogen chloride, hydrogen bromide, sulfuric acid or polyphosphoric acid.

5. The process according to claim 1, wherein the reaction is effected at 50°-150° C.

6. The process according to claim 2, wherein the reaction is effected in the presence of hydrogen chloride.

7. The process according to claim 6, wherein the reaction is effected in a combination system of an alcohol and hydrogen chloride.

* * * * *